United States Patent

Wells

Patent Number: 5,160,333
Date of Patent: Nov. 3, 1992

[54] METHOD FOR MIXING BLOOD WITH ANTICOAGULANT

[75] Inventor: John R. Wells, Culver City, Calif.

[73] Assignee: Solco Hospital Products Group, Inc., Hingham, Mass.

[21] Appl. No.: 649,831

[22] Filed: Feb. 1, 1991

[51] Int. Cl.$^5$ ............................................. A61M 1/00
[52] U.S. Cl. ...................................... 604/408; 604/4; 604/317; 604/405
[58] Field of Search .................................. 604/4–6, 604/403–416

[56] References Cited

U.S. PATENT DOCUMENTS

| | | | |
|---|---|---|---|
| 3,304,977 | 2/1967 | Hammons | 604/408 |
| 4,146,172 | 3/1979 | Cullis et al. | 604/6 |
| 4,301,799 | 11/1981 | Pope, Jr. et al. | 604/405 |
| 4,443,220 | 4/1984 | Hauer et al. | 604/408 |
| 4,781,707 | 11/1988 | Boehringer et al. | 604/317 |
| 4,787,898 | 11/1988 | Raines | 604/411 |
| 4,846,795 | 7/1989 | Minagawa | 604/410 |

Primary Examiner—Robert A. Hafer
Assistant Examiner—Kerry Owens
Attorney, Agent, or Firm—Donald G. Lewis

[57] ABSTRACT

A method for mixing blood with anticoagulant in conjunction with an autologous blood transfusion system employs a mixing tube for directing the blood to the bottom of a blood bag.

4 Claims, 1 Drawing Sheet

METHOD FOR MIXING BLOOD WITH ANTICOAGULANT

The invention relates to blood bags. More particularly, the invention relates to methods for mixing blood with anticoagulant within a blood bag.

BACKGROUND OF THE INVENTION

When blood is drawn into a blood bag, it is necessary to mix the blood with anticoagulant in order to prevent clotting. Conventionally, anticoagulant is preloaded into the blood bag before the blood is drawn. As the blood is then drawn into the bag, the bag may be periodically inverted or agitated so as to mix the incoming blood with the anticoagulant.

The task of mixing blood with anticoagulant can become more problematic if the user is unable to invert or agitate the blood bag. For example, incorporation of the blood bag into an autologous blood transfusion system may hinder the user's ability to invert the bag. One type of autologous blood transfusion system (Solco Basle Inc., Rockland MA) encloses the blood bag within a rigid evacuated chamber. Blood is then drawn or aspirated into the blood bag through a port at the top of the bag by evacuating the blood bag itself. During the blood drawing procedure, there is a tendency for the drawn blood to layer on top of anticoagulant within the blood bag. The port for evacuating the blood bag also lies near the top of the bag. Accordingly, during the blood drawing procedure, the blood bag may not be inverted so as to mix the blood with anticoagulant because, to do so, would cause blood to be drawn from the blood bag and into the vacuum line connected thereto. Clogging the vacuum line with blood is considered undesirable for a variety of reasons. Similarly, there is a risk that agitating the blood bag may cause blood to splash onto the evacuation port. Partial mixing may be achieved by gently rocking the blood bag. Such gentle rocking poses only a minimal risk of clogging the vacuum line. However, the mixing efficiency of such gentle rocking progressively declines as the blood bag approaches fullness.

An alternative arrangement for an autologous blood transfusion device is disclosed by Marx, U.S. Pat. No. 4,573,992. Marx discloses that blood may be aspirated into the bottom of an evacuated blood bag. If Marx's blood bag were preloaded with anticoagulant, mixing of such anticoagulant with drawn blood would be assured if air were periodically allowed to pass through the aspiration port. Unfortunately, it is possible for such aeration to cause blood to foam and/or denature.

What was needed was a method for automatically mixing blood with anticoagulant within a blood bag without inverting or agitating the blood bag and without causing the blood to foam.

SUMMARY

The invention discloses a device and method for mixing blood with anticoagulant within a blood bag by means of a mixing tube. The blood bag is of a type which includes both an aspiration port and an evacuation port. Both ports are located at the top of the bag. Blood may be drawn into the blood bag by activating a vacuum to the evacuation port and supplying the aspiration port with a source of blood. The mixing tube is attached to the aspiration port and serves to direct the aspirated blood toward the bottom of the blood bag. If the bag is preloaded with anticoagulant, the mixing tube serves to direct the aspirated blood into the anticoagulant and to mix the blood therewith. In an alternative embodiment, the mixing tube also serves to deflect the flow of blood laterally along the bottom of the blood bag so as to enhance its mixing with the anticoagulant. In order to prevent air from bubbling through the blood when the blood bag is partially full, i.e. when the tip of the mixing tube is submerged within the drawn blood, another alternative embodiment of the mixing tube includes one or more shunting orifices at or near its proximal end adjacent to its attachment with the aspiration port so as to allow air to be drawn from the mixing tube without passing through the tip.

Figures 4, 5:
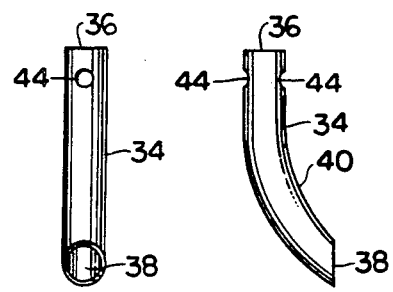
FIG. 4 is a perspective view of an alternative embodiment of a preferred mixing tube.
FIG. 5 is a perspective view of the mixing tube of FIG. 4 rotated 90 degrees illustrating its curvature or hook configuration.

FIGS.'s 6–8 are sectional views of an autologous blood transfusion device having a mixing tube of the type shown in FIG. 4 and illustrating the preferred method of mixing blood with anticoagulant.

Figure 6:
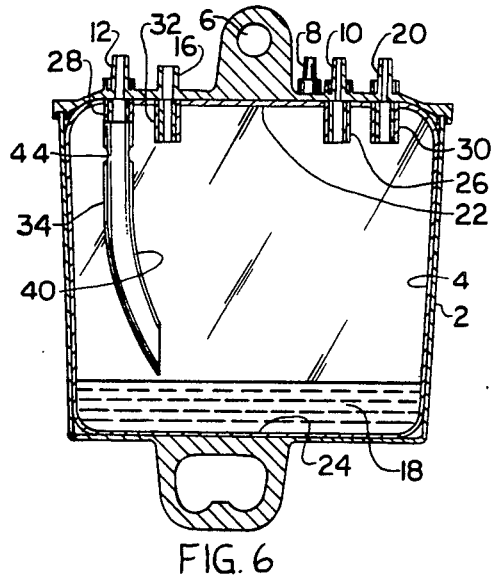

FIG. 6 illustrates a blood bag within an autologous blood transfusion device containing preloaded anticoagulant.

Figure 7:
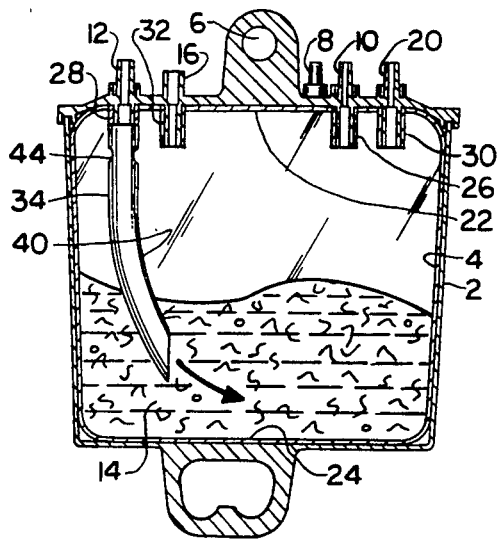

FIG. 7 illustrates the process of aspirating blood into the blood bag.

Figure 8:
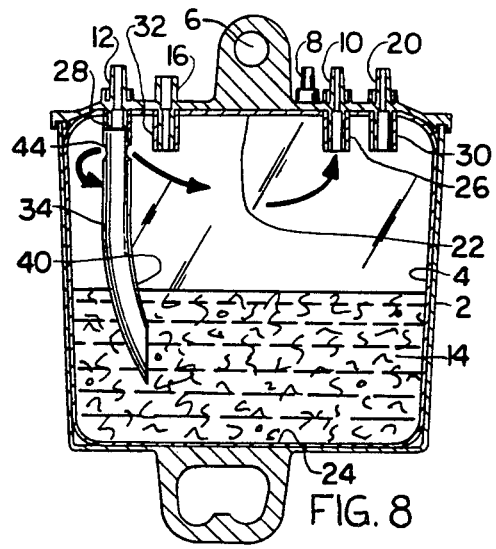

FIG. 8 illustrates the process of venting air through shunting orifices near the top of the mixing tube so as to prevent air from bubbling through the blood when the tip of the mixing tube is submerged therein.

Figures 1, 2, 3:
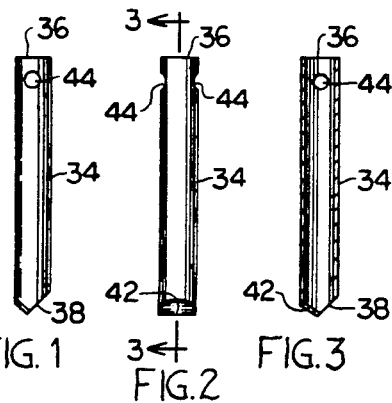
FIG. 1 is a perspective view of a preferred mixing tube.
FIG. 2 is a perspective view of the mixing tube of FIG. 1 rotated 90 degrees.
FIG. 3 is a sectional view of the mixing tube of FIG. 2.
Figure 9:
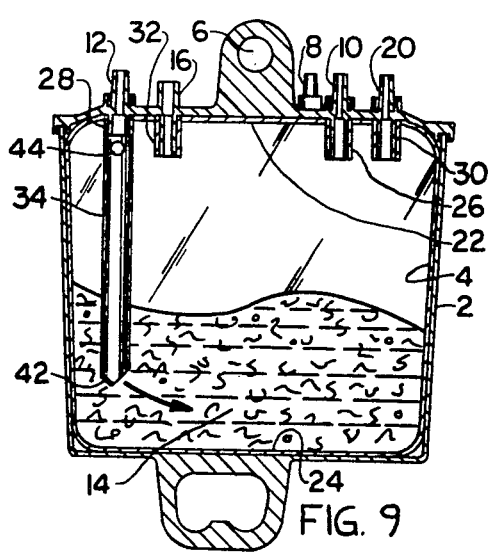

FIG. 9 is a sectional view of an autologous blood transfusion device having a mixing tube of the type shown in FIG. 1 illustrating the lateral deflection of blood as it is aspirated into the bottom of the blood bag.

DETAILED DESCRIPTION OF THE INVENTION

The invention is best described in the context of its use within an autologous blood transfusion device. A preferred embodiment of the invention as incorporated within an autologous blood transfusion device is illustrated in FIGS. 6–8. The autologous blood transfusion device includes a rigid chamber (2) for housing the blood bag (4). The rigid chamber (2) has sufficient strength to be evacuated without collapsing. Preferably, the rigid chamber (2) has a composition, at least in part, of clear plastic so as to enable the user to view the state of the blood bag (4) contained therein. During the blood drawing procedure, the rigid chamber (2) may be maintained in an upright position by suspension on a hook or other means (6). The rigid chamber (2) illustrated in FIGS. 6–8 is in its upright position. The rigid chamber (2) may include an external port (8). This external port (8) may be connected to a vacuum source for evacuating the rigid chamber (2). The rigid chamber (2) may also include various connectors (10,12,16,20). A first connector (10) may be coupled to a vacuum source and employed for evacuating air from the blood bag (4).

A second connector (12) may be connected to a blood source and employed for aspirating blood (14) into the blood bag (4). A third connector (16) may be connected to a source of anticoagulant (18) and employed for passing anticoagulant (18) into the blood bag (4) prior to the blood drawing procedure. And a fourth connector (20) may be connected to drainage tubing and employed for draining the blood (14) from the blood bag (4) during the transfusion procedure. During the transfusion procedure, the rigid chamber (2) is inverted so as to allow the blood (14) within the blood bag (4) to drain from this fourth connector (20). To facilitate the drainage of blood (14) from the blood bag (4), the rigid chamber (2) may be elevated and vented by opening the external port (8). Alternatively, the drainage of blood (14) from the blood bag (4) may be facilitated by pressurizing the rigid chamber (2) by connecting the external port (8) to a source of pressurized air. In either case, the flow rate of the infusion should be regulated so as to comply with standard medical procedures.

The blood bag (4) has a flexible plastic composition compatible with blood (14). In the preferred embodiment, the autologous blood transfusion device is supplied to the consumer with the rigid chamber (2) evacuated and the blood bag (4) expanded therein. Accordingly, the expanded shape of the blood bag (4) should be adapted to fit the interior shape of the rigid chamber (2). The blood bag (4) has a top portion (22) and a bottom portion (24), defined by its orientation within the rigid chamber (2) when the rigid chamber (2) is in its upright position, as illustrated in FIGS. 6-8. The top portion (22) of the blood bag (4) has several ports (26,28,30,32) incorporated therein. In FIGS. 6-8, these ports (26,28,30,32) are illustrated as inwardly protruding sleeves. However, the ports (26,28,30,32) may also take other configurations. The first port (26) may be connected to the first connector (10) of the rigid chamber (2) and may be employed for evacuating air from the blood bag (4). The second port (28) may be connected to the second connector (12) of the rigid chamber (2) and employed for aspirating blood (14) into the blood bag (4). The third port (30) may be connected to the third connector (16) of the rigid chamber (2) and employed for introducing anticoagulant (18) into the blood bag (4) prior to the blood drawing procedure. And the fourth port (32) may be connected to the fourth connector (20) of the rigid chamber (2) and employed for draining the blood (14) from the blood bag (4) during the transfusion procedure.

A preferred embodiment of the mixing tube (34) is shown in FIGS. 4 and 5 and is illustrated in FIGS. 6-8. The mixing tube (34) has a proximal end (36) and a distal end (38). The proximal end (36) of the mixing tube (34) is "joined" to the second port (28) of the blood bag (4). In the preferred embodiment, the mixing tube (34) may be joined to the second port (28) of the blood bag (4) by attaching to the second connector (12) of the rigid chamber (2) and abutting or substantially abutting the second port (28). Alternatively, the mixing tube (34) may be joined to the second port (28) by extending directly therefrom or by being welded or otherwise attached thereto. As a further alternative, the mixing tube (34) may be incorporated as an extension or attachment to the second connector (12). The distal end (38) of the mixing tube (34) is open and extends within the blood bag (4) so as to conduct blood (14) with force toward the bottom portion (24) of the blood bag (4).

Prior to the blood aspiration procedure, the blood bag (4) may be preloaded with anticoagulant (18). The anticoagulant (18) will collect at the bottom (24) of the blood bag (4). During the blood drawing procedure, without the mixing tube (34), the aspirated blood (14) tends to drip from the second port (28) onto the layer of anticoagulant (18). During the latter stages of the blood drawing procedure, there is a tendency for the aspirated blood (14) dripping from the second port (28) to layer itself above the previously aspirated blood (14) without mixing with the anticoagulant (18). With the employment of the mixing tube (34), the aspirated blood (14) is released with force into the blood bag (4) proximal to the bottom (24) so as to facilitate mixing with the anticoagulant (18).

The preferred embodiment of the mixing tube (34), as illustrated in FIGS. 4-8, includes a means for laterally deflecting aspirated blood (14) along the bottom of the blood bag (4). In the embodiment illustrated in FIGS. 4-8, the mixing tube (34) includes a hooked configuration (40) which serves as the deflecting means. In an alternative embodiment, as illustrated in FIGS. 1-3 and FIG. 9, the distal end (38) of the mixing tube (34) includes a deflecting surface (42) which serves to deflect the aspirated blood (14) laterally within the blood bag (4).

In an alternative preferred embodiment, the mixing tube (34) may include one or more shunting orifices (44) as illustrated in FIGS. 1-9. Without the shunting orifice (44), when the distal end (38) of the mixing tube (34) is submerged in drawn blood (14), air which is aspirated along with the blood (14) will also pass through the distal end (38) of the mixing tube (34) along with the aspirated blood (14) and may cause the drawn blood (14) to bubble and or foam. It is considered medically undesirable for blood (14) to foam prior to reinfusion. Accordingly, the shunting orifice (44) is added to the mixing tube (34) in order to shunt air which is drawn into the mixing tube (34) before it can bubble through the drawn blood (14) within the blood bag (4). The shunting orifice (44) is located near the proximal end (36) of the mixing tube (34) and serves to vent air therefrom. The vented air passes through the top portion (22) of the blood bag (4) and is evacuated out the first port (26) into the vacuum source. The shunting orifice (44) aids in the prevention of air discharging through blood (14) in the bottom (24) of the blood bag (4) when the distal end (38) of the mixing tube (34) is submerged within such blood (14).

The invention also includes methods which employ the mixing tube (34) for mixing blood (14) with anticoagulant (18). In a preferred method, the mixing tube (34) is employed in a blood drawing procedure. Firstly, air is evacuated from the rigid chamber (2) so as to expand the blood bag (4) contained therein. Then anticoagulant (18) can be preloaded into the blood bag (4) via the third connector (16) or port (30). The anticoagulant (18) will collect at the bottom (24) of the blood bag (4). Then, in preparation for the aspiration of blood (14) into the blood bag (4), air may be evacuated from the blood bag (4). Air may be evacuated from the blood bag (4) by connecting the first connector (10) or port (26) to a vacuum source. Once the blood bag (4) is evacuated, blood (14) may be drawn into the blood bag (4). The blood is aspirated from a patient or other blood source as part of a surgical or other medical procedure. The aspirated blood (14) passes through the second port (28) and into the mixing tube (34) connected thereto. The mixing tube (34) extends toward the bottom (24) of the blood bag (4) and directs the aspirated blood (14) thereto. In an alternative method, the aspirated blood (14) is conducted proximate to the bottom of the blood bag (4) and is then deflected laterally thereinto. The aspirated blood (14) is directed or laterally deflected with force proximal to the bottom of the blood bag (4) by means of a mixing tube (34) so as to cause the aspirated blood (14) to mix with anticoagulant (18).

In an alternative method, foaming of the drawn blood (14) within the blood bag (4) caused by bubbling aspirated air through the distal end (38) of the mixing tube (34) while such mixing tube is submerged within drawn blood (14) is abated by the use of one or more shunting orifices (44) near the proximal end (36) of the mixing tube (34). The shunting orifices (44) allow aspirated air to pass directly from the mixing tube (34) into the upper portion (22) of the blood bag (4). The aspirated air is then evacuated from the blood bag (4) through the first connector (10) and into the vacuum source.

What is claimed is:

1. A method for mixing blood with anticoagulant comprising the following steps:
    Step A: evacuating air from a rigid container and expanding a blood bag contained therein;
    Step B: preloading anticoagulant into the blood bag;
    Step C: evacuating air from the blood bag within the rigid container; and then
    Step D: drawing blood into the blood bag and directing the blood toward the bottom of the blood bag with force by means of a mixing tube so as to mix the blood with the anticoagulant.

2. A method for mixing blood with anticoagulant as described in claim 1 comprising the following additional step subsequent to said Step C:
    Step E: shunting air from the mixing tube via a shunting orifice at the proximal end of the mixing tube for abating the passage of air bubbles through the blood drawn into the blood bag.

3. A method for mixing blood with anticoagulant comprising the following steps:
    Step A: evacuating air from a rigid container and expanding a blood bag contained therein;
    Step B: preloading anticoagulant into the blood bag;
    Step C: evacuating air from the blood bag within the rigid container; and then
    Step D: drawing blood into the blood bag, and deflecting the blood laterally near the bottom of the blood bag with force by means of a mixing tube so as to mix the blood with the anticoagulant.

4. A method for mixing blood with anticoagulant as described in claim 3 comprising the following additional step subsequent to said Step C:
    Step E: shunting air from the mixing tube via a shunting orifice at the proximal end of the mixing tube for abating the passage of air bubbles through the blood drawn into the blood bag.

* * * * *